United States Patent [19]

Adachi et al.

[11] 4,138,259
[45] Feb. 6, 1979

[54] COLOR PHOTOGRAPHIC LIGHT-SENSITIVE MATERIAL

[75] Inventors: Keiichi Adachi; Tadao Shishido; Hiroshi Hara; Shigeo Hirano, all of Minami-ashigara, Japan

[73] Assignee: Fuji Photo Film Co., Ltd., Minami-ashigara, Japan

[21] Appl. No.: 846,469

[22] Filed: Oct. 28, 1977

[30] Foreign Application Priority Data

Oct. 29, 1976 [JP] Japan .................. 51/130768

[51] Int. Cl.$^2$ .................. G03C 1/76; G03C 1/40
[52] U.S. Cl. .................. 96/74; 96/56; 96/100 R
[58] Field of Search .................. 96/100, 56, 74

[56] References Cited

U.S. PATENT DOCUMENTS

| | | | |
|---|---|---|---|
| 3,432,300 | 3/1969 | Lestina et al. | 96/56 |
| 3,574,627 | 4/1971 | Stern et al. | 96/56 |
| 3,764,337 | 10/1973 | Arai et al. | 96/56 |
| 3,930,866 | 1/1976 | Oishi et al. | 96/56 |
| 3,982,944 | 9/1976 | Ohi et al. | 96/56 |

Primary Examiner—J. Travis Brown
Attorney, Agent, or Firm—Sughrue, Rothwell, Mion, Zinn and Macpeak

[57] ABSTRACT

A color photographic silver halide light-sensitive material capable of providing color images having excellent fastness and free from discoloration at the non-image areas comprising a support having thereon a silver halide photographic emulsion layer having a dye image providing material associated therewith and with the light-sensitive material containing at least one compound represented by the following general formula (I) or a precursor thereof:

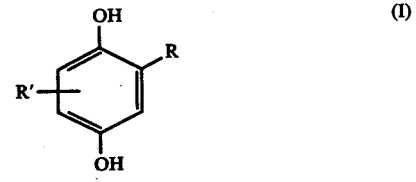

wherein R and R', which may be the same or different, each represents

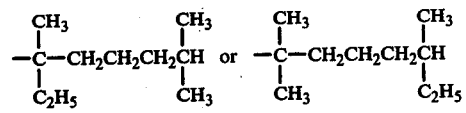

and at least one phenolic compound having an ether bond at the 4-position thereof.

20 Claims, No Drawings

COLOR PHOTOGRAPHIC LIGHT-SENSITIVE MATERIAL

BACKGROUND OF THE INVENTION

1. Field of the Invention

The present invention relates to a color photographic light-sensitive material and, more particularly, it relates to preventing fading of the dye images ultimately obtained by development processing a color photographic light-sensitive material and preventing discoloration of uncolored areas (hereinafter referred to as white background).

2. Description of the Prior Art

Color photographic light-sensitive materials are, in general, prepared by coating on an appropriate support a silver halide emulsion containing couplers dispersed therein. Conventional color photographic light-sensitive materials are produced by dispersing couplers capable of forming cyan, magenta and yellow dyes upon coupling with the oxidation products of color developing agents into red-sensitive, green-sensitive and blue-sensitive silver halide emulsions, respectively, and coating these emulsions in an appropriate order on a support.

Color photographic light-sensitive materials thus produced are subjected, after exposure, to a series of processing steps such as color development, bleaching, fixing, stabilizing, etc., to ultimately form color images.

Recently, an intensification process in which color dye images having the same optical density are formed, but using several tenths of the amount of silver halide present in an ordinary light-sensitive material, has been developed. A cobalt (III) complex salt and a peroxide are known as intensifying agents. In such a processing, silver images and color dye images are formed in a color development step just as in a conventional process and dyes are further formed in a subsequent intensifying bath by the reaction of a coupler with a color developing agent, which is present in the photographic material, oxidized with an intensifying agent in the presence of image-wise distributed silver as a catalyst. After bleaching and fixing steps, the dye images remaining in the photographic material comprise azomethine dyes or indoaniline dyes. Therefore, the color images thus obtained are in substance the same as color images formed in a conventional manner.

Color photographic images thus-obtained are stored for a long period of time as records or to be displayed. However, these photographic images are not necessarily stable to light, humidity or heat and, when exposed to light for a long period of time, the dye images tend to fade or discolor and, in addition, the white background is also discolored, usually resulting in a deterioration of image quality. Such a phenomenon is enhanced when the dye images are exposed to light or stored under high temperature and high humidity conditions.

This fading and discoloration of images are fatal defects in a recording material. The following compounds have heretofore been used to remove these defects. For example, hydroquinone derivatives including 2,5-di-tert-butylhydroquinone, phenol compounds such as 2,6-di-tert-butyl-p-cresol, 4,4'-methylenebis(2,6-di-tert-butylphenol), 2,2'-methylenebis(4-ethyl-6-tert-butylphenol), 4,4'-isopropylidenediphenol, etc., and tocopherols are representative of such compounds.

These compounds are effective to some extent as an agent which prevents fading or discoloration of dye images. However, the effect is not completely satisfactory or, although some compounds may prevent fading, they deteriorate the hue, cause fog, reduce dispersion property or form crystals. Thus, satisfactory color image stabilizers which exhibit completely excellent effects for photographic use are not known.

Methods for improving these disadvantages are disclosed in Japanese Patent Application (OPI) No. 14023/1976 and U.S. Pat. No. 3,930,866, in which a phenolic compound as described in U.S. Pat. Nos. 3,432,300, 3,573,050, 3,574,627 and 3,930,866, British Pat. No. 1,347,556 is used together with a hydroquinone derivative. However, even with these somewhat improved methods, the prevention of fading or discoloration of dye images and the stability of the dispersion are still insufficient. Further, most of the hydroquinone derivatives used in the above described methods have the disadvantages that two to four reaction steps are required for their preparation, that a high reaction temperature or a long reaction time is necessary when a few reaction steps are involved and that the dispersion containing the hydroquinone derivatives per se has insufficient stability, etc.

SUMMARY OF THE INVENTION

An object of the present invention is to provide a stable dispersion in which a novel hydroquinone derivative and a phenolic compound are used in combination.

Another object of the present invention is to provide a color silver halide photographic material having a silver halide photographic emulsion layer with a dye image providing material and the material containing in a photographic layer thereof a dispersion of this hydroquinone derivative and a phenolic compound which does not deteriorate the hue, which does not cause fog, which can stabilize color images to a better extent than known techniques and which exhibits collectively excellent effects for photographic use.

As a result of various investigations, it has now been discovered that the objects of the present invention are attained by the incorporation in at least one photographic layer of a color photographic light-sensitive material of at least one hydroquinone derivative represented by the following general formula (I) or a precursor thereof:

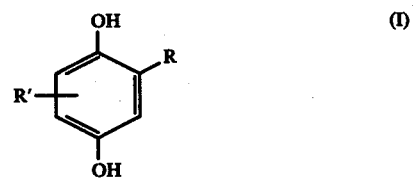

wherein R and R', which may be the same or different, each represents

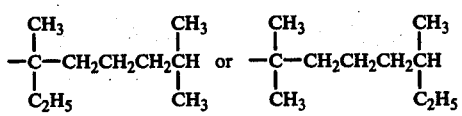

together with at least one phenolic compound having an ether bond at the 4-position thereof.

DETAILED DESCRIPTION OF THE INVENTION

The term "precursor" as used herein means a compound capable of releasing upon hydrolysis the hydroquinone derivative of the general formula (I) above. For example, a hydroquinone derivative wherein the hydrogen atom of one or both of the hydroxyl groups in the hydroquinone nucleus are substituted with an acyl group (with the term "acyl group" being used herein in its broad sense and including, for example,

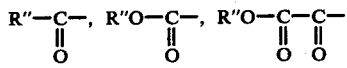

(wherein R" represents an aliphatic group such as an alkyl group), etc.) is considered to be such a precursor.

The hydroquinone derivatives of this invention of the general formula (I) can, in general, be prepared by reacting hydroquinone and 3,7-dimethyloctan-3-ol in a suitable solvent for dissolving the hydroquinone and in the presence of a catalyst at a temperature of about 40° to about 100° C. for a period of about 2 hours to about 7 hours.

In this reaction, 3,7-dimethyloctan-3-ol is used in an excess molar amount to that of the hydroquinone. Suitable solvents which can be used include alcohols, e.g., methanol, ethanol, methyl Cellosolve and the like, and a suitable amount thereof ranges from about 100 to about 300 ml/mol of hydroquinone. In addition, suitable catalysts which can be used include Lewis acids, e.g., sulfuric acid, phosphoric acid, boron trifluoride, etc.

Specific examples of the synthesis of the hydroquinone derivative of the general formula (I) are described below. Unless otherwise indicated herein, all parts, percents, ratios and the like are by weight.

SYNTHESIS EXAMPLE 1

55 g of hydroquinone and 216 ml of 3,7-dimethyloctan-3-ol were dissolved in 100 ml of methanol. Then, 100 ml of concentrated sulfuric acid (36 N) was added dropwise thereto under stirring and cooling so that the temperature did not rise above 50° C. Subsequently, the reaction mixture was maintained at 55° C. to 60° C. for 4 hours. Then, the reaction mixture was added to ice-water, and extracted with 500 ml of benzene. The benzene layer was washed with water and, after drying over anhydrous sodium sulfate, benzene and unreacted 3,7-dimethyloctan-3-ol were distilled off. The residual oily product was distilled under reduced pressure to obtain 134 g of an oily product having a boiling point of 209° to 220° C./1.9 mm Hg. The oily product was determined to be 2,5-bis(1-ethyl-1,5-dimethylhexyl)hydroquinone through elemental analysis and infrared absorption spectral analysis.

Elemental Analysis — Calcd. (%) for $C_{26}H_{46}O_2$: C 79.94; H 11.87. Found (%): C 79.87; H 11.87.

SYNTHESIS EXAMPLE 2

55 g of hydroquinone and 71.5 g of 3,7-dimethyloctan-3-ol were dissolved in 100 ml of methanol. Then, 50 ml of concentrated sulfuric acid (36 N) was added dropwise thereto under stirring and cooling so as to maintain the temperature at 40° C. or less. Subsequently, the reaction mixture was maintained at 50° to 55° C. for 4 hours. The resulting reaction mixture was added to ice-water, and extracted with 500 ml benzene. The benzene layer was washed with water and, after drying over anhydrous sodium sulfate, benzene and unreacted 3,7-dimethyloctan-3-ol were distilled off under reduced pressure. The residual oil was chromatographed on silica gel using benzene as a developing solvent. Thus, 29.8 g of 2,5-bis(1-ethyl-1,5-dimethylhexyl)hydroquinone (the same compound as obtained in Synthesis Example 1) was first eluted, and then 15.1 g of 2-(1-ethyl-1,5-dimethylhexyl)hydroquinone was eluted.

Elemental Analysis — Calcd. (%) for $C_{16}H_{26}O_2$: C 76.75; H 10.47. Found (%): C 76.88; H 10.48.

In the above-described Synthesis Example 2, 2,5-bis(1-ethyl-1,5-dimethylhexyl)hydroquinone and 2-(1-ethyl-1,5-dimethylhexyl)hydroquinone were produced in a weight proportion of about 2:1. The effects of the present invention can be obtained using this mixture as such.

Further, by changing the relative amount of 3,7-dimethyloctan-3-ol to hydroquinone and controlling the reaction temperature and the reaction time, a mixture of monoalkylhydroquinone and a dialkylhydroquinone in an optional portion thereof can be obtained.

In addition, mass spectral data suggest that the hydroquinone derivatives obtained in Synthesis Examples 1 and 2 each comprised a mixture of isomers thereof wherein the alkyl group in one isomer was a 1,1,5-trimethylheptyl group and the alkyl group in the other isomer was a 1-ethyl-1,5-dimethylhexyl group. Furthermore, it was found from NMR data that isomers wherein the alkyl groups are substituted at the 2- and 6-positions are present in a slight amount. An additional isomer is 2(1-ethyl-1,5-dimethylhexyl)-5-(1,1,5-trimethylheptyl)hydroquinone.

Examples of phenolic compounds having an ether bond at the 4-position thereof (hereinafter phenolic compound) which can be used in the present invention include alkoxyphenols, aryloxyphenols, hydroxycoumarans, hydroxychromans, dihydroxyspirochromans, etc.

Preferred phenolic compounds are those compounds represented by the following general formulae (IIa) to (IIc):

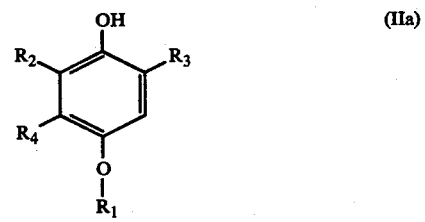

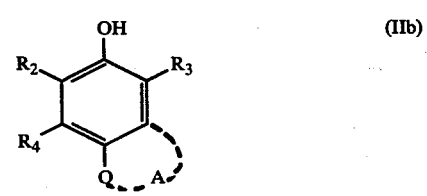

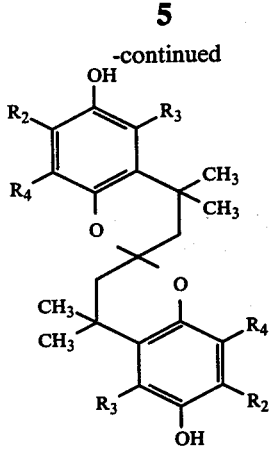
(IIc)

wherein $R_1$ represents a straight chain, branched chain or cyclic alkyl group (such as a methyl group, a tert-butyl group, a hexyl group, an octyl group, a tert-octyl group, an octadecyl group, etc.); a substituted straight chain or branched chain alkyl group (such as a 1-ethoxycarbonyltridecyl group, 1-N-phenylcarbamoyltridecyl group, etc.); a mono- or bicyclic aryl group (such as a phenyl group, etc.); an aralkyl group in which the aryl moiety is a monocyclic aryl moiety and the alkyl moiety is a straight chain or branched chain alkyl moiety (such as a benzyl group, a phenethyl group, etc.); or a terphenyl group (such as a 7,7-dimethylnorbornyl group, etc.); $R_2$, $R_3$ and $R_4$, which may be the same or different, each represents a hydrogen atom; a straight chain, branched chain or cyclic alkyl group (such as a methyl group, a tert-butyl group, a cyclopentyl group, a cyclohexyl group, an octyl group, a dodecyl group, an octadecyl group, etc.); a straight chain or branched chain alkoxy group (such as a methoxy group, a butoxy group, a dodecyloxy group, etc.); a straight chain or branched chain alkylthio group (such as an octylthio group, a hexadecylthio group, an octadecylthio group, etc.); a monocyclic aryl group (such as a phenyl group, etc.); a monocyclic aryloxy group (such as a phenoxy group, etc.); an aralkyl group in which the aryl moiety is a monocyclic aryl moiety and the alkyl moiety is a straight chain or branched chain alkyl moiety (such as a benzyl group, a phenethyl group, etc.); an aralkoxy group in which the aryl moiety is a monocyclic aryl moiety and the alkyl moiety is a straight chain or branched chain alkyl moiety (such as a benzyloxy group, a phenethyloxy group, etc.); a straight chain or branched chain alkenyl group (such as an allyl group, etc.); a straight chain or branched chain alkenoxy group (such as allyloxy group, etc.); an acylamino group (such as an acetylamino group, a benzoylamino group, etc.); or a halogen atom (such as a chlorine atom, etc.); and A represents the non-metallic atoms necessary for completing a 5-membered or 6-membered ring containing a

grouping and the ring can be substituted with a straight chain, branched chain or cyclic alkyl group (such as a methyl group, a tert-butyl group, a cyclohexyl group, an octyl group, a dodecyl group, an octadecyl group, etc.); a straight chain or branched chain alkoxy group (such as a methoxy group, a butoxy group, a dodecyloxy group, etc.); a monocyclic aryl group (such as a phenyl group, etc.); a monocyclic aryloxy group (such as a phenoxy group, etc.); an aralkyl group in which the aryl moiety is a monocyclic aryl moiety and the alkyl moiety is a straight chain or branched chain alkyl moiety (such as a benzyl group, a phenethyl group, etc.); an aralkoxy group in which the aryl moiety is a monocyclic aryl moiety and the alkyl moiety is a straight chain or branched chain alkyl moiety (such as a benzyloxy group, a phenethyloxy group, etc.); a straight chain or branched chain alkenyl group (such as an allyl group, etc.); a straight chain or branched chain alkenoxy group (such as an allyloxy group, etc.); an N-substituted amino group (such as an N-alkylamino group, a di-(N-alkyl)amino group, an N-alkyl-N-arylamino group, a piperazino group, a morpholino group, etc.); or a heterocyclic ring (such as a benzothiazolyl ring, a benzoxazolyl ring, an imidazolyl ring, an oxazolyl ring, etc.). Furthermore, the above-described ring can be substituted with a residue forming a condensed ring. Also, the alkyl group and the aryl group as described above for $R_1$ to $R_4$ and as substituents can be substituted with one or more of a halogen atom, a hydroxyl group, a carboxyl group, an alkoxycarbonyl group, an acyloxy group, a carbamoyl group, a sulfo group, a sulfonyloxy group, an amido group (e.g., an acetamido group, an ethanesulfonamido group, a benzamido group, etc.), an alkoxy group or an aryloxy group.

The phenolic compounds of the general formula (IIa) in which the total number of carbon atoms of $R_1$, $R_2$, $R_3$ and $R_4$ is larger than 8, the phenolic compounds of the general formula (IIb) in which the total number of carbon atoms of $R_2$, $R_3$, $R_4$ and A is larger than 8, and the phenolic compounds of the general formula (IIc) have the property of low diffusibility and hence are suitable for positioning selectively in a specific hydrophilic layer of the color photographic material. Also, the phenolic compounds having a total number of carbon atoms of up to about 40 are suitable for ordinary purposes.

Particularly useful examples of the phenolic compounds which can be used in the present invention are the 5-hydroxycoumarans and the 6-hydroxychromans which are compounds of the general formula (IIb) where one of $R_2$ and $R_3$ is a hydrogen atom and also the 6,6'-dihydroxy-bis-2,2'-spirochromans represented by the general formula (IIc).

Specific examples of the phenolic compounds which can be used in the present invention are shown below.

(PH-1)

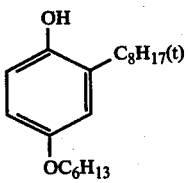

(PH-2) 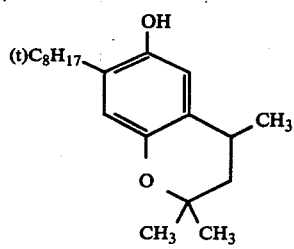
(PH-3) 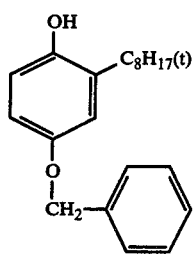
(PH-4) 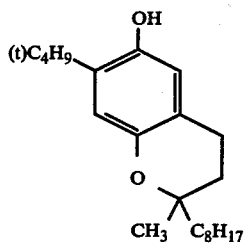
(PH-5) 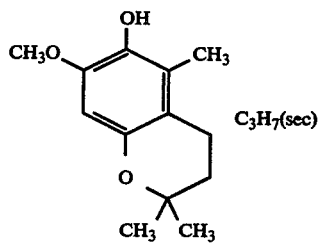
(PH-6) 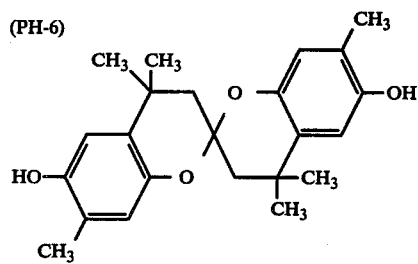
(PH-7) 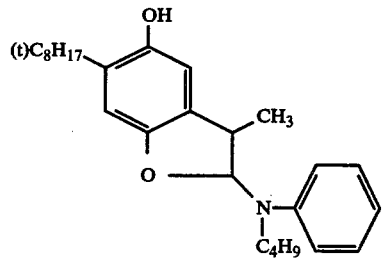
(PH-8) 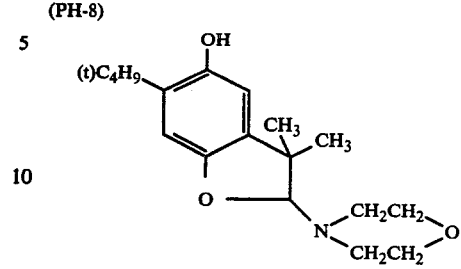
(PH-9) 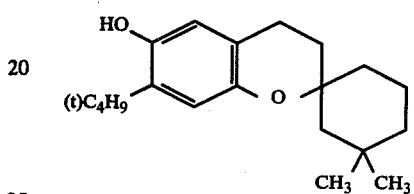
(PH-10) 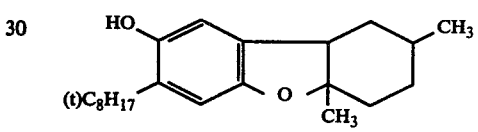
(PH-11) 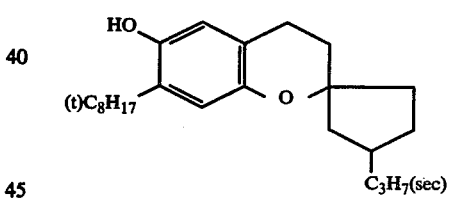
(PH-12) 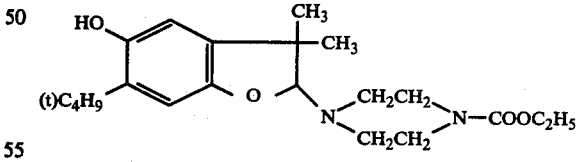
(PH-13) 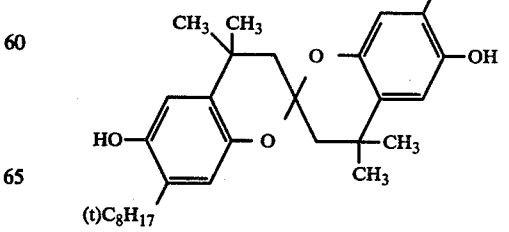

-continued (PH-14)
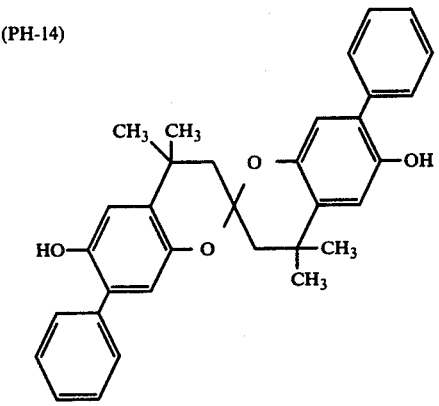

(PH-15)
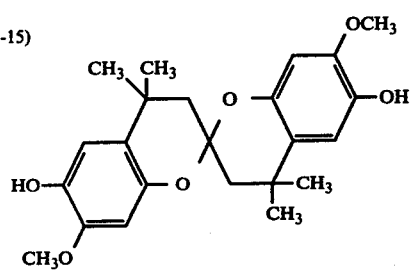

(PH-16)
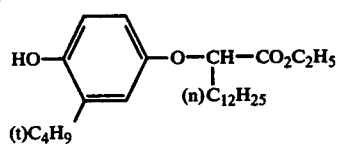

(PH-17)
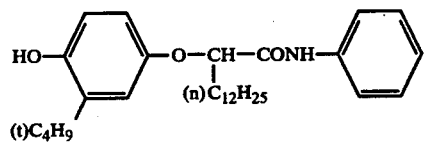

(PH-18)
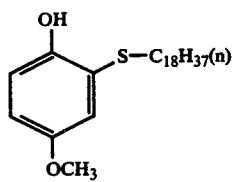

(PH-19)
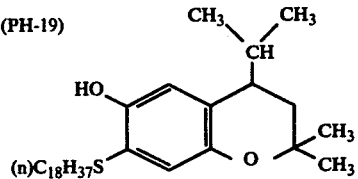

The phenolic compound which can be used in the present invention can be prepared according to the methods described, for example, in U.S. Pat. Nos. 2,535,058, 3,184,457, 3,285,937 and 3,432,300, German Patent Application (OLS) Nos. 2,005,301, 2,008,376, 2,140,309, 2,146,668 and 2,165,371.

The photographic layer of a color photographic light-sensitive material which contains a compound represented by the general formula (I) and a phenolic compound having an ether bond at the 4-position according to the present invention includes various hydrophilic protective colloid layers, for example, a silver halide light-sensitive emulsion layer, a protective layer, a yellow filter layer, an antihalation layer, a subbing layer, an intermediate layer, a color diffusion transfer positive layer, etc.

The compound represented by the general formula (I) and the phenolic compound having an ether bond at the 4-position which can be used in the present invention can be employed individually or as a combination thereof or further can be used together with coupler(s) by dissolving them in a high-boiling organic solvent with or without an auxiliary solvent and forming a dispersion thereof. A suitable molar ratio of the compound represented by the general formula (I) to the phenolic compound ranges from about 0.1:1 to about 10:1, preferably 0.2:1 to 5:1.

The high-boiling organic solvent used in the present invention is an organic solvent which has a boiling point of above 170° C. and which is immiscible with water. Typical examples of high boiling organic solvents include dibutyl phthalate, dinonyl phthalate, butyl benzoate, diethylhexyl sebacate, butyl stearate, dinonyl maleate, tributyl citrate, tricresyl phosphate, dioctylbutyl phosphate, trihexyl phosphate, etc., as described in U.S. Pat. Nos. 3,676,137 and 2,322,027, diethyl succinate, dioctyl adipate, 3-ethylbiphenyl, the liquid dye stabilizers described, as improved photographic dye image stabilizers, in *Product Licensing Index*, Vol. 83, pp. 26-29 (March, 1971)

Examples of low boiling organic solvents which can be used as auxiliary solvents together with a high boiling organic solvent include ethyl acetate, butyl acetate, ethyl propionate, ethyl formate, butyl formate, nitroethane, carbon tetrachloride, chloroform, hexane, cyclohexane, ethylene glycol, acetone, ethanol, dimethylformamide, dioxane, etc. In addition, benzene, toluene, xylene, etc., can also be used with these solvents. These solvents are described, for example, in U.S. Pat. Nos. 2,801,171, 2,801,170 and 2,949,360.

Surface active agents can also be used in dispersing a solution of the color image stabilizer (the compound of the general formula (I) and the phenolic compound) individually or in combination with a coupler in an aqueous protective colloid solution. Illustrative examples of suitable surface active agents include saponin, sodium alkylsulfosuccinates, sodium alkylbenzenesulfonates, etc., and examples of hydrophilic protective colloids which can be used are gelatin, casein, carboxymethyl cellulose, polyvinyl alcohol, polyvinyl pyrrolidone, styrene-maleic anhydride copolymers, condensates of styrene-maleic anhydride copolymers and polyvinyl alcohol, polyacrylic acid salts, ethyl cellulose, etc. However, the present invention is not to be construed to be limited only to these examples.

To incorporate the compound of the general formula (I) and the phenolic compound which can be used in the present invention into a silver halide light-sensitive layer, the compounds can be dissolved in a low boiling organic solvent such as ethyl acetate, methanol, etc., and directly add the solution thereof to a mixture of a silver halide emulsion and a coupler dispersion. However, it is desirable to dissolve the compounds of the present invention in a high boiling organic solvent such as dibutyl phthalate, tricresyl phosphate, etc., together with a coupler, disperse the solution into a hydrophilic protective colloid such as gelatin and add the dispersion to a silver halide emulsion, or to add a dispersion of the color image stabilizers alone and a coupler dispersion to a silver halide emulsion.

Although the compound of the general formula (I) and the phenolic compound which can be used in the present invention are effective for preventing fading or discoloration of magenta, yellow or cyan color images and preventing discoloration of a white background, they are particularly effective for preventing fading or discoloration of magenta images and preventing a yellow discoloration of a white background. Further, a dispersion of the compound of the general formula (I) and the phenolic compound, with or without a coupler, is very stable in practical use and only very slight crystal deposition occurs. Thus, the use of the combination of this invention is superior to known methods in which a hydroquinone derivative or a phenolic derivative is used alone.

The compound of the general formula (I) and the phenolic compound used in the present invention each is suitably employed in an amount of about 0.5 to about 200% by weight, preferably 2 to 150% by weight, based on the weight of the couplers, although the amount thereof will vary some depending upon the kind of couplers employed.

If the compound of the general formula (I) or the phenolic compound is employed in an amount less than about 0.5% by weight, an extremely poor effect in preventing fading or discoloration of color images and discoloration of background are achieved and thus such is practically unsuitable. On the other hand, if the compound of the general formula (I) or the phenolic compound is used in an amount larger than about 200% by weight, such can inhibit the progress of development and may cause a reduction of color density.

In practicing the present invention, known anti-fading agents can be used together with the compound of the general formula (I) and the phenolic compound. Known anti-fading agents which can be used include, for example, hydroquinone derivatives described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921, Japanese Patent Application 69148/1976, etc., gallic acid derivatives described in U.S. Pat. Nos. 3,457,079 and 3,069,262, Japanese Patent Publication 13496/1968, etc. A suitable amount of known anti-fading agent which can also be used is an amount up to substantially the same molar amount of the phenolic compound of this invention.

Illustrative examples of couplers which can be used in the present invention include the following couplers.

Examples of yellow couplers which can be used generally include open-chain ketomethylene compounds such as those described in, e.g., U.S. Pat. Nos. 3,341,331, 2,875,057, 3,551,155, German Patent Application (OLS) No. 1,547,868, U.S. Pat. Nos. 3,265,506, 3,582,322, 3,725,072, German Patent Application (OLS) No. 2,162,899, U.S. Pat. Nos. 3,369,895, 3,408,194, German Patent Application (OLS) Nos. 2,057,941, 2,213,461, 2,219,917, 2,261,361, 2,263,875, etc.

Suitable magenta couplers which can be used include mainly 5-pyrazolone compounds. In addition, indazolone compounds and cyanoacetyl compounds can also be used. Examples of suitable magenta couplers are described in, e.g., U.S. Pat. Nos. 2,439,098, 2,600,788, 3,062,653, 3,558,319, British Pat. No. 956,261, U.S. Pat. Nos. 3,582,322, 3,615,506, 3,519,429, 3,311,476, 3,419,391, 3,935,015, German Patent Application (OLS) No. 2,424,467, German Pat. No. 1,810,464, Japanese Patent Publication 2016/1969, German Patent Application (OLS) No. 2,418,959, Japanese Patent Application 118540/1975, U.S. Pat. No. 2,983,608, German Patent Application (OLS) Nos. 2,532,225, 2,536,191, Japanese Patent Application (OPI) No. 16924/1976, etc.

Of the magenta couplers which can be used in the present invention, magenta couplers providing particularly advantageous effects are represented by the following general formulae (III) and (IV):

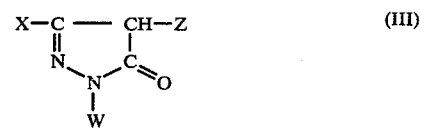

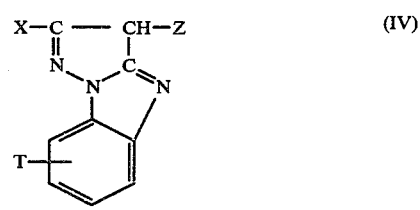

wherein W represents a hydrogen atom or a group with 1 to 35 carbon atoms, preferably 1 to 22 carbon atoms, which includes a straight chain or branched chain alkyl group (for example, a methyl, isopropyl, tert-butyl, hexyl, dodecyl, etc., group), an alkenyl group (for example, an allyl, etc., group), a cycloalkyl group (for example, a cyclopentyl, cyclohexyl, norbornyl, etc., group), an aralkyl group (for example, a benzyl, β-phenylethyl, etc., group) and a cycloalkenyl group (for example, a cyclopentenyl, cyclohexenyl, etc., group); which groups can be substituted with one or more substituents such as a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group and a mercapto group.

Further, W represents an aryl group (for example, a phenyl, α- or β-naphthyl, etc., group) and an aryl group having one or more substituent(s). Suitable substituents for the aryl group include an alkyl group, an alkenyl group, a cycloalkyl group, an aralkyl group, a cycloalkenyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group and a mercapto group. A phenyl group in which at least one of the ortho-positions is substituted with an alkyl group, an alkoxy group or a halogen atom is particularly useful for W, since, when the coupler remains in a color photographic material after development, less printout due to the action of light or heat occur.

Furthermore, W represents a heterocyclic group (for example, a 5-membered or 6-membered heterocyclic group or a condensed heterocyclic group containing one or more of a nitrogen atom, an oxygen atom or a sulfur atom as a hetero atom, such as a pyridyl, quinolyl, furyl, benzothiazolyl, oxazolyl, imidazolyl, naphthoxazolyl, etc., group) or a heterocyclic group substituted with one or more of the substituents above-described for the aryl group for W.

Furthermore, W represents an acyl group, a thioacyl group, an alkylsulfonyl group, an arylsulfonyl group, an alkylsulfinyl group, a carbamoyl group or a thiocarbamoyl group.

In the formulae, X represents a hydrogen atom or a group having 1 to 35 carbon atoms, preferably 1 to 22 carbon atoms, which includes a straight chain or branched chain alkyl group, an alkenyl group, a cycloalkyl group, an aralkyl group and a cycloalkenyl group, which groups can be substituted with one or more substituents as above-described for W.

Further, X represents an aryl group or a heterocyclic group which can be substituted with one or more substituents as described for W.

Furthermore, X represents an alkoxycarbonyl group (for example, a methoxycarbonyl, ethoxycarbonyl, stearyloxycarbonyl, etc., group), an aryloxycarbonyl group (for example, a phenoxycarbonyl, α- or β-naphthoxycarbonyl, etc., group), an aralkyloxycarbonyl group (for example, a benzyloxycarbonyl, etc., group), an alkoxy group (for example, a methoxy, ethoxy, dodecyloxy, etc., group), an aryloxy group (for example, a phenoxy, tolyloxy, etc., group), an alkylthio group (for example, an ethylthio, dodecylthio, etc., group), an arylthio group (for example, a phenylthio, α-naphthylthio, etc., group), a carboxy group, an acylamino group (for example, an acetamido, 3-[(2,4-di-tert-amylphenoxy)acetamido]benzamido, etc., group), a diacylamino group, an N-alkylacylamino group (for example, an N-methylpropionamido, etc., group), an N-arylacylamino group (for example, an N-phenylacetamido, etc., group), a ureido group (for example, a ureido, N-arylureido, N-alkylureido, etc., group), a thioureido group (for example, a thioureido, N-arylthioureido, N-alkylthioureido, etc., group), a urethane group, a thiourethane group, an anilino group (for example, a phenylamino, N-alkylanilino, N-arylanilino, N-acylanilino, 2-chloro-5-tetradecanamidoanilino, etc., group), an alkylamino group (for example, an N-butylamino, N,N-dialkylamino, cycloalkylamino, etc., group), a cycloamino group (for example, a piperidino, pyrrolidino, etc., group), an alkylcarbonyl group (for example, a methylcarbonyl, etc., group), an arylcarbonyl group (for example, a phenylcarbonyl, etc., group), a sulfonamido group (for example, an alkylsulfonamido, arylsulfonamido, etc., group), a carbamoyl group (for example, an N-alkylcarbamoyl, (N,N-dialkylcarbamoyl, N-alkyl-N-arylcarbamoyl, N-arylcarbamoyl, N,N-diarylcarbamoyl, etc., group), a sulfamoyl group (for example, an N-alkylsulfamoyl, N,N-dialkylsulfamoyl, N-arylsulfamoyl, N-alkyl-N-arylsulfamoyl, N,N-diarylsulfamoyl, etc., group), a guanidino group (for example, an N-alkylguanidino, N-arylguanidino, etc., group), a cyano group, an acyloxy group (for example, a tetradecanoyloxy, etc., group), an sulfonyloxy group (for example, a benzenesulfonyloxy, etc., group), a hydroxy group, a mercapto group, a halogen atom or a sulfo group.

In the formula, T represents a hydrogen atom or a group having 1 to 35 carbon atoms, preferably 1 to 22 carbon atoms, which includes a straight chain or branched chain alkyl group, an alkenyl group, a cycloalkyl group, an aralkyl group, and a cycloalkenyl group, which can be substituted with one or more substituents as described above for these groups for W.

Further, T represents an aryl group or a heterocyclic group which can be substituted with one or more substituents as described above for these groups for W.

Furthermore, T represents a halogen atom, a cyano group, an alkoxy group, an aryloxy group, a carboxy group, an alkoxycarbonyl group, an aryloxycarbonyl group, an acyloxy group, an alkylcarbonyl group, an arylcarbonyl group, an alkylthiocarbonyl group, an arylthiocarbonyl group, a sulfo group, a sulfamoyl group, a carbamoyl group, a ureido group, a thioureido group, a diacylamino group, a ureido group, a thioureido group, a urethane group, a thiourethane group, a sulfonamido group, an alkylsulfonyloxy group, an arylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group or a mercapto group.

Z represents a hydrogen atom or a group bonded directly to the coupling position and capable of being released by the coupling reaction with an oxidation product of a primary amine developing agent.

The coupling-off group represented by Z can be a coupling-off group bonded to the coupling position through an oxygen atom, a nitrogen atom or a sulfur atom.

More specifically, Z represents a coupling-off group in which an alkyl group, an aryl group, a sulfonyl group, a sulfinyl group, a carbonyl group, a phosphoric acid group, a thiocarbonyl group, a heterocyclic group or a cyano group is bonded to an oxygen atom, a nitrogen atom or a sulfur atom which is directly bonded to the coupling position or a coupling-off group forming a 5- or 6-membered nitrogen-containing ring in which the nitrogen atom thereof is directly bonded to the coupling position.

Preferred coupling-off groups for Z which are bonded to the coupling position through an oxygen atom include, for example, an acyloxy group, an aryloxy group, an alkoxy group, a hydroxamato group, a carbonato group, an oxalato group, a heterocyclic oxy group, a phosphato group, a thiophosphato group, a carbamoyloxy group, a thiocarbamoyloxy group, an oxamoyloxy group, a thiooxamoyloxy group and the like.

Preferred coupling-off groups for Z which are bonded to the coupling position through a sulfur atom include, for example, a thiocyano group, an alkylthio group, an arylthio group, a heterocyclic thio group, an alkylsulfinyl group, an arylsulfinyl group, a heterocyclic sulfinyl group, an alkylsulfonyl group, an arylsulfonyl group, a heterocyclic sulfonyl group, a sulfo group, an alkylsulfonylthio group, an arylsulfonylthio group, a disulfido group, a sulfido group, a thiocarbamato group, a dithiocarbamato group, a thiocarbonato group, a dithiocarbonato group and the like.

Preferred coupling-off groups for Z which are bonded to the coupling position through a nitrogen atom include, for example, an acylamino group, a diacylamino group, a sulfonamido group, a sulfinamido group, an alkylamino group, an arylamino group, a uredio group, a thioureido group, a phosphoric amido group, a urethane group, a thioacylamino group, an isocyanato group, and the like, and a nitrogen containing 5- or 6-membered heterocyclic ring (for example, a cycloamino ring such as pyrrolidine, morpholine, piperazine, indoline, piperidine, etc., a cyclic diacylamino ring such as phthalimido, succinimido, saccharin, oxazolidone, thiohydantoin, hydantoin, etc., a cycloamido ring such as pyridone, oxazolidone, phthalide, valerolactam, etc., an aromatic cycloamino ring such as imidazole, pyrrole, benzotriazole, etc.) and the like.

Phenol or naphthol derivatives are predominantly used as cyan couplers. Suitable examples of cyan couplers are described in, e.g., U.S. Pat. Nos. 2,369,929, 2,474,293, 2,698,794, 2,895,826, 3,311,476, 3,458,315, 3,560,212, 3,582,322, 3,591,383, 3,386,301, 2,434,272, 2,706,684, 3,034,892, 3,583,971, German Patent Application (OLS) No. 2,163,811, Japanese Patent Publication No. 28836/1970, Japanese Patent Application No. 33238/1973, etc.

In addition, couplers capable of releasing a development inhibitor upon color coupling (the so-called DIR couplers) or compounds capable of releasing a development inhibiting compound may also be employed. Examples of these compounds are described in, e.g., U.S. Pat. Nos. 3,148,062, 3,227,554, 3,253,924, 3,617,291, 3,622,328, 3,705,201, British Pat. No. 1,201,110, U.S. Pat. Nos. 3,297,445, 3,379,529, 3,639,417, etc.

Colored couplers can also be used in the present invention, and examples are illustrated in U.S. Pat. Nos. 2,434,272, 3,476,564, 3,476,560, Japanese Patent Application No. 45971/1973, U.S. Pat. Nos. 3,034,892, 3,386,301, 2,434,272, 3,148,062, 3,227,554, 3,701,783, 3,617,291, etc.

Preferred examples of yellow couplers useful in the present invention are illustrated below.

α-{3-[α-(2,4-Di-tert-amylphenoxy)butyramido]-benzoyl}-2-methoxyacetanilide

α-Acetoxy-α-3-[γ-(2,4-di-tert-amylphenoxy)-butyramido]benzoyl-2-methoxyacetanilide N-(4-Anisoylacetamidobenzenesulfonyl)-N-benzyl-N-toluidine α-(2,4-Dioxo-5,5-dimethyloxazolyzin-3-yl)-α-pivaloyl-2-chloro-5-[α-(2,4-di-tert-amylphenoxy)-butyramido]-acetanilide α-(4-Carboxyphenoxy)-α-pivaloyl-2-chloro-5-[α-(2,4-di-tert-amylphenoxy)butyramido]acetanilide α-(1-Benzyl-2,4-dioxohydantoin-3-yl)-α-pivaloyl-2-chloro-5-[α-(2,4-di-tert-amylphenoxy)-butyramido]acetanilide α-(4-Methoxybenzoyl)-α-(3,5-dioxomorpholino)-5-[γ-(2,4-di-tert-amylphenoxy)butyramido]-2-chloroacetanilide α-(2,4-Dioxo-5,5-dimethyloxazolidin-2-yl)-α-pivaloyl-2-chloro-5-(hexadecylsulfonylamino)acetanilide α-(1-Benzyl-5-ethoxy-2,4-dioxohydantoin-3-yl)-α-pivaloyl-2-methoxy-5-(tetradecyloxycarbonyl)acetanilide α-(2,4-Dioxo-5,5-dimethylhydantoin-3-yl)-α-pivaloyl-2-chloro-5-[α-(2,4-di-tert-amylphenoxy)-butyramido]acetanilide α-(1-Benzyl-2,4-dioxo-5-ethoxyhydantoin-3-yl)-α-pivaloyl-2-chloro-5-(hexadecylsulfonylamino)acetanilide α-(1-Methyl-2,4-dioxo-5-methoxyhydantoin-3-yl)-α-pivaloyl-2-methoxy-5-[N-γ-(2,4-di-tert-amylphenoxy)-propylsulfamoyl]acetanilide α-(1-Benzyl-2,4-dioxo-5-phenylhydantoin-3-yl)-α-pivaloyl-2-chloro-5-[γ-(2,4-di-tert-amylphenoxy)-butyramido]acetanilide α-(5,5-Dimethyl-2,4-dioxooxazolidin-3-yl)-α-pivaloyl-2-chloro-5-[γ-(2,4-di-tert-amylphenoxy)-butyramido]actanilide α-(1-Benzyl-2,4-dioxo-5-ethoxyhydantoin-3-yl)-α-pivaloyl-2-chloro-5-dodecyloxycarbonylacetanilide α-(1-Carboxymethyl-2,4-dioxohydantoin-3-yl)-α-pivaloyl-2-chloro-5-[(2,4-di-tert-amylphenoxy)acetamido]acetanilide α-(N-Phthalimido)-α-pivaloyl-2-chloro-5-hexadecyloxycarbonylacetanilide α-(2,4-Dioxo-5,5-dimethylhydantoin-3-yl)-α-(4-methoxybenzoyl)-2-chloro-5-[γ-(2,4-di-tert-amylphenoxy)butyramido]acetanilide α-(N-Phthalimido)-α-benzoyl-2-methoxy-5-(tetradecyloxycarbonyl)acetanilide α-(1-Benzyl-2,4-dioxo-5-ethoxyhydantoin-3-yl)-α-(4-methoxybenzoyl)-2-chloro-5-[α-(2,4-di-tert-amylphenoxy)butyramido]acetanilide α-(1-Methyl-2,4-dioxo-5-methoxyhydantoin-3-yl)-α-(2-methylbenzoyl)-2-chloro-5-(dodecyloxycarbonyl)acetanilide α-(2,4-Dioxo-5,5-dimethyloxazolidin-3-yl)-α-{3-[(2,4-di-tert-amylphenoxy)acetamido]benzoyl}-2-methoxyacetanilide Preferred examples of magenta couplers useful in the present invention are illustrated below.

1-(2,4,6-Trichlorophenyl)-3-[3-(2,4-di-tert-amylphenoxyacetamido)benzamido]-5-pyrazolone 1-(2,4,6-Trichlorophenyl)-3-{3-[α-(2,4-di-tert-amylphenoxyacetamido]benzamido}-4-acetoxy-5-pyrazolone 1-(2,4,6-Trichlorophenyl)-3-tetradecanamido-4-(4-hydroxyphenylazo)-5-pyrazolone 1-(2,4,6-Trichlorophenyl)-3-[2-chloro-5-tetradecanoylamino)anilino]-5-pyrazolone 1-(2,4,6-Trichlorophenyl)-3-(2-chloro-5-tetradecyloxycarbonyl)anilino-4-(1-naphthylazo)-5-pyrazolone 1-(2,4-Dichloro-6-methoxyphenyl)-3-[(2-chloro-5-tetradecanoylamino)anilino]-4-benzyloxycarbonyloxy-5-pyrazolone 1-(2,4,6-Trichlorophenyl)-3-{3-[(2,4-di-tert-amylphenoxy)acetamido]benzamido}-4-piperidino-5-pyrazolone 1-(2,4,6-Trichlorophenyl)-3-{2-chloro-5-[α-(2,4-di-tert-amylphenoxy)butyramido]anilino}-4-N-phthalimido-5-pyrazolone 1-(2,4,6-Trichlorophenyl)-3-[(2-chloro-5-tetradecanoylamino)anilino]-4-(3-methyl-4-hydroxyphenylazo)-5-pyrazolone 2-{3-[α-(2,4-Di-tert-amylphenoxy)butyramido]-benzamido}-7-chloropyrazolo-[1,5a]-benzimidazole Preferred examples of cyan couplers useful in the present invention are illustrated below.

1-Hydroxy-N-[γ-(2,4-di-tert-amylphenoxy)propyl]-2-naphthamide

1-Hydroxy-4-[2-(2-hexyldecyloxycarbonyl)phenylazo]-2-[N-(1-naphthyl)naphthamide

1-Hydroxy-4-chloro-N-[α-(2,4-di-tert-amylphenoxy)butyl]-2-naphthamide

5-Methyl-4,6-dichloro-2-[α-(3-n-pentadecylphenoxy)-butyramido]phenol

1-Hydroxy-4-[2-(ethoxycarbonyl)phenylazo]-N-(2-ethylhexyl)-2-naphthamide

The stabilizing effect of the present invention on a color image is particularly remarkable when a magenta coupler of the couplers which can be used in the present invention is used.

In order to incorporate the coupler into a silver halide emulsion layer, known methods, for example, the method described in U.S. Pat. No. 2,322,027, can be used. That is, the coupler is dissolved in an organic solvent, for example, an alkyl ester of phthalic acid (such as dibutyl phthalate, dioctyl phthalate, etc.), an ester of phosphoric acid (such as diphenyl phosphate, triphenyl phosphate, tricresyl phosphate, dioctyl butyl phosphate, etc.), an ester of citric acid (such as tributyl acetyl citrate, etc.), an ester of benzoic acid (such as octyl benzoate, etc.), an alkylamide (such as N,N-diethyllaurylamide, etc.), and the like, or in an organic solvent having a boiling point of about 30° to about 150° C., for example, a lower alkyl acetate (such as ethyl acetate, butyl acetate, etc.), ethyl propionate, secondary butyl alcohol, methyl isobutyl ketone, β-ethoxyethyl acetate, methyl Cellosolve acetate, and the like, and then the solution is dispersed in a hydrophilic colloid. The high boiling organic solvent and the low boiling organic solvent described above can be used in admixture, if desired.

A coupler having an acid group such as a carboxylic acid group or a sulfonic acid group can be incorporated in a hydrophilic colloid as an aqueous alkaline solution thereof.

These couplers are generally used in an amount from about $2 \times 10^{-3}$ to about $5 \times 10^{-1}$ mol, preferably from $1 \times 10^{-2}$ to $5 \times 10^{-1}$ mol per mol of the silver in the emulsion layer.

Gelatin is advantageously used as the hydrophilic protective colloid which can be used in a photographic layer but other hydrophilic protective colloids can also be used. For example, a gelatin derivative, a graft polymer of gelatin and another polymer, a protein such as albumin, casein, etc., a cellulose derivative such as hydroxyethylcellulose, carboxymethylcellulose, cellulose sulfate, sodium alginate, a saccharide derivative such as a starch derivative and many kinds of synthetic hydrophilic high molecular weight materials such as a homopolymer or copolymer of polyvinyl alcohol, polyvinyl alcohol partial acetal, poly-N-vinyl pyrrolidone, polyacrylic acid, polymethacrylic acid, polyacrylamide, polyvinyl imidazole, polyvinyl pyrazole, etc., are illustrative.

In addition to alkali treated gelatin, acid treated gelatin, a hydrolyzed product of gelatin, and an enzyme treated gelatin can be used as the gelatin.

Gelatin derivatives which can be used are those which are obtained by reacting gelatin with various kinds of compounds, for example, an acid halide, an acid anhydride, an isocyanate, a bromoacetic acid, an alkanesultone, a vinylsulfonamide, a maleinimide compound, a polyalkylene oxide, an epoxy compound. Specific examples of gelatin derivatives are described in U.S. Pat. Nos. 2,614,928, 3,132,945, 3,186,846 and 3,312,553, British Pat. Nos. 861,414, 1,033,189 and 1,005,784, Japanese Patent Publication No. 26845/1967, etc.

Gelatin graft polymers which can be used are those which are obtained by grafting a polymer or copolymer of vinyl monomers such as acrylic acid, methacrylic acid, or an ester or an amide derivative thereof, acrylonitrile, styrene, etc., to gelatin. Particularly preferred polymers are those compatible with gelatin to some extent, e.g., polymers of acrylic acid, methacrylic acid, acrylamide, methacrylamide, and hydroxyalkyl methacrylates, etc. Examples of these compounds are described in U.S. Pat. Nos. 2,763,625, 2,831,767 and 2,956,884, etc.

Typical synthetic hydrophilic high molecular weight materials are described, for example, in German Patent Application (OLS) No. 2,312,708, U.S. Pat. Nos. 3,620,751 and 3,879,205, Japanese Patent Publication 7561/1968, etc.

The photographic emulsion used in the present invention can contain any silver halide such as silver bromide, silver iodobromide, silver iodochlorobromide, silver chlorobromide and silver chloride.

The grain size distribution can be narrow or broad. The silver halide grains in the photographic emulsion can have a regular crystal form such as that of a cubic or octahedral system, an irregular crystal form such as that of a spherical or plate-like system, or can be a mixed system thereof. A mixture of grains having various kinds of crystal forms can be used.

The crystal structure of the silver halide grains can be uniform throughout the grains, or can be heterogenous with the interior and the exterior differing from each other. Further, the silver halide grains can be of the type which forms a latent image predominately on the surface of the grains or can be of the type which forms a latent image predominately in the interior of the grains.

The photographic emulsion used in the present invention can be prepared using the methods described in P. Grafkides, *Chimie et Physique Photographique*, Paul Montel, Paris (1967), G. F. Duffin, *Photographic Emulsion Chemistry*, The Focal Press, London (1966), V. L. Zelikman, et al., *Making and Coating Photographic Emulsions*, The Focal Press, London (1964), etc. That is, the emulsion can be prepared using an acid process, a neutral process or an ammonia process. Further, any system for mixing a water-soluble silver salt and a water-soluble halide, such as a single jet adding method, a double jet adding method, a mixture thereof can be used.

A method in which the silver halide grains are formed in the presence of excess silver ion (the so-called reverse mixing method) can also be used. A method of the double jet adding method in which the pAg of the liquid phase wherein the silver halide grains are formed is maintained at constant, i.e., the so-called controlled double jet method can be used. According to this method, a silver halide emulsion containing silver halide grains having a regular crystal form and a homogeneous grain size distribution can be obtained.

Also, two or more silver halide emulsions which are prepared separately can be used in mixture, if desired.

During the preparation of the silver halide grains or the process of physical ripening, a cadmium salt, a zinc salt, a lead salt, a thallium salt, an iridium salt, a complex salt thereof, a rhodium salt, a complex salt thereof, an iron salt, a complex salt thereof can be present.

In the production of the photographic light-sensitive materials according to the present invention, a photographic emulsion layer and other hydrophilic colloid layers can be coated on a support or on another layer using various known coating methods including dip coating, roller coating, curtain coating, extrusion coating, etc. The methods described in U.S. Pat. Nos. 2,681,294, 2,761,791 and 3,526,528 can be advantageously used.

Suitable supports which can be used in the present invention include those which are commonly used for photographic light-sensitive materials such as a cellulose nitrate film, a cellulose acetate film, a cellulose acetate butyrate film, a cellulose acetate propionate film, a polystyrene film, a polyethylene terephthalate film, a polycarbonate film, a laminate of these films, a thin glass film, paper, and the like. Papers coated or laminated with baryta or an α-olefin polymer, in particular, a polymer of an α-olefin having 2 to 10 carbon atoms, such as polyethylene, polypropylene, an ethylene-butene copolymer, etc., synthetic resin films whose surface has been roughened to improve the adhesive property with other polymers as described in Japanese Patent Publication No. 19068/1972 also provide good results.

Suitable supports include transparent or opaque supports which are selected depending upon the end-use of the light-sensitive materials. Also, transparent supports colored with a dye or pigment can be used as well.

In practicing the present invention, it is naturally additionally effective and advantageous to prevent fading or discoloration by light to provide an ultraviolet light-absorbing layer on the upper surface of a photographic light-sensitive image-forming layer upon coating on a support.

The present invention is not limited by the kinds of conventionally used color processing agents such as color developing agents, bleaching agents, fixing agents, etc. Also, the present invention is not limited by the kind of intensifying agents to be used for color intensifying processing, e.g., as described in German Patent Application (OLS) No. 181,390, Japanese Patent Application (OPI) No. 9728/1973, Japanese Patent Application No. 128327/1974, etc.

The present invention is applicable to conventional color light-sensitive materials, in particular, to color light-sensitive materials for printing. Also, it is applicable to silver-saving type color light-sensitive materials described in U.S. Pat. Nos. 3,765,890, 3,902,905, 3,674,490 and 3,761,265, etc. Further, the present invention is applicable to the color photographic system described in U.S. Pat. Nos. 3,227,550, 3,227,551, 3,227,552, U.S. Provisional Patent Publication U.S.B. 351,673, etc., in particular, to the color diffusion transfer photographic system.

Color photographic development processing is necessary after exposure in order to obtain dye images using the color photographic light-sensitive material of the present invention. Color photographic development processing fundamentally involves a color developing step, a bleaching step, and a fixing step. In some cases, two of these steps can be conducted in a single processing. In addition, a combination of a color development, a first fixing and a bleach-fixing is also possible. The development processing step is combined with, if necessary, a prehardening bath, a neutralizing bath, a first development (black-and-white development), an image-stabilizing bath, a washing or the like. A suitable processing temperature is in many cases about 18° C. or above. Particularly, the processing temperature can be about 20° C. to 60° C., and more recently about 30° C. to about 60° C.

A suitable color developer solution which can be used in an alkaline aqueous solution having a pH of about 8 or higher, preferably 9 to 12, containing a color developing agent. Preferred typical examples of the above-described color developing agent are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline, and the salts thereof (e.g., sulfates, hydrochlorides, sulfites, p-toluenesulfonates, etc.). Other examples are described in U.S. Pat. Nos. 2,193,015, 2,592,364, Japanese Patent Application (OPI) No. 64933/1973, L.F.A. Mason, *Photographic Processing Chemistry*, pp. 226–229, Focal Press, London (1966), etc. The above-described compounds may be used together with 3-pyrazolidones, if desired.

If desired, various additives may be added to the color developer solution.

The color developer solution can further contain pH buffers such as alkali metal sulfites, carbonates, borates or phosphates, development inhibitors or anti-fogging agents such as bromides, iodides or organic anti-fogging agents.

Specific examples of anti-fogging agents include potassium bromide, potassium iodide, nitrobenzimidazoles described in U.S. Pat. Nos. 2,496,940 and 2,656,271, mercaptobenzimidazole, 5-methylbenzotriazole, 1-phenyl-5-mercaptotetrazole, the compounds described in U.S. Pat. Nos. 3,113,864, 3,342,596, 3,295,976, 3,615,522, 3,597,199, etc., the thiosulfonyl compounds described in British Pat. No. 972,211, the phenazine-N-oxides as described in Japanese Patent Publication No. 41675/1971, the anti-fogging agents described in *Kagaku Shashin Binran*, Vol. II, pp. 29–47, and the like.

In addition, the color developer may contain, if desired, a water softener, a preservative such as hydroxylamine, an organic solvent such as benzyl alcohol, diethylene glycol, etc., a development accelerator such as polyethylene glycol, a quaternary ammonium salt, an amine, etc., a dye-forming coupler, a competing coupler, a fogging agent such as sodium borohydride, an auxiliary developing agent such as 1-phenyl-3-pyrazolidone, a viscosity-imparting agent, and the like.

After color development processing, the photographic emulsion layer is usually subjected to bleaching. Bleaching may be conducted either simultaneously with fixing or independently thereof. Suitable bleaching agents which can be used include compounds of multivalent metals such as iron (III), cobalt (III), chromium (VI), copper (II), etc., peracids, quinones, nitroso compounds, etc. For example, ferricyanides, dichromates, organic complex salts of iron (III) or cobalt (III), complex salts of aminopolycarboxylic acids (e.g., ethylenediaminetetraacetic acid, nitrilotriacetic acid, 1,3-diamino-2-propanoltetraacetic acid, etc.) or of organic acids (e.g., citric acid, tartaric acid, malic acid, etc.), persulfates, permanganates, nitrosophenol, etc., can be used. Of these, potassium ferricyanide, iron (III) sodium ethylenediaminetetraacetate and iron (III) ammonium ethylenediaminetetraacetate are particularly useful. Ethylenediaminetetraacetic acid-iron (III) complex salt is effective in a bleaching solution and in a monobath bleach-fixing solution.

Various additives including the bleaching-accelerators described in U.S. Pat. Nos. 3,042,520, 3,241,966, Japanese Patent Publication Nos. 8506/1970, 8836/1970, etc., can be added to the bleaching solution or bleach-fixing solution.

The present invention is illustrated in greater detail by reference to the following typical examples thereof.

EXAMPLE 1

10 g of 1-(2,4,6-trichlorophenyl)-3-(2-chloro-5-tetradecanamido)anilino-2-pyrazolin-5-one (as a magenta coupler), 2 g of Compound PH-1 and 2 g of the compound prepared in Synthesis Example 1 were dissolved in a mixture of 5 ml of tricresyl phosphate and 20 ml of ethyl acetate, and the resulting solution was dispersed in 100 g of a 10% gelatin aqueous solution containing sodium dodecylbenzenesulfonate. Then, this dispersion was mixed with 145 g of a silver chlorobromide emulsion (Br: 70 mol%) (containing 7 g of silver) and, after adding thereto a hardener and a coating aid, the emulsion was coated on a paper support, both sides of which were laminated with polyethylene, and dried to prepare Sample 1. The coated amount was 400 mg/m² in terms of the coupler.

In the same manner, Sample 2 and Sample 3 were prepared using 2 g of the compound prepared in Synthesis Example 2 and 2 g of 2,5-di-tert-octylhydroquinone in place of the compound prepared in Synthesis Example 1, respectively.

After exposing these samples for 1 second to light of 1,000 lux, they were processed with the following processing solutions.

| Color Developer Solution | |
|---|---|
| Benzyl Alcohol | 15 ml |
| Na$_2$SO$_3$ | 5 g |
| KBr | 0.4 g |
| Hydroxylamine Sulfate | 2.0 g |
| 4-Amino-3-methyl-N-ethyl-N-β-(methanesulfonamido)ethylaniline | 10.0 g |
| Na$_2$CO$_3$ | 30.0 g |
| Diethylenetriaminepentaacetic Acid | 5.0 g |
| Water to make | 1,000 ml |
| | (pH 10.1) |
| Bleach-Fixing Solution | |
| Ammonium Thiosulfate (70% aq. soln.) | 150 ml |
| Na$_2$SO$_3$ | 15 g |
| Na[Fe(EDTA)] | 40 g |
| EDTA | 4 g |
| Water to make | 1,000 ml |
| | (pH 6.8) |

| Processing Step | Temperature (° C) | Time |
|---|---|---|
| Color Development | 33 | 3 min 30 sec |
| Bleach-Fixing | 33 | 1 min 30 sec |
| Washing | 28–35 | 3 min |

Each of the thus-obtained samples containing dye images was subjected to a fading test for 4 weeks using a fluorescent lamp fading tester (20,000 lux) equipped with an ultraviolet light-absorbing filter absorbing light of a wavelength of 400 nm or shorter (made by Fuji Photo Film Co., Ltd.). The results obtained are shown in Table 1 below.

Table 1

| Sample | Yellow Density Change in Background Areas | Magenta Density Change in Areas of Initial Density 1.0 |
|---|---|---|
| 1* | +0.05 | −0.30 |
| 2* | +0.05 | −0.30 |
| 3** | +0.05 | −0.45 |

*Present Invention
**Comparison

The results in the above Table show that with the phenolic compound having an ether bond in the 4-position thereof, the same effects are obtained from the compound of the general formula (I) prepared in Synthesis Example 1 and the compound of the general formula (I) prepared in Synthesis Example 2, and that Samples 1 and 2 containing the combination of phenolic compound having an ether bond in the 4-position thereof with the compound of the general formula (I) according to the present invention exhibit a lesser increase in stain due to light and the color images have a superior light-fastness in comparison with Sample 3 containing 2,5-di-tert-octylhydroquinone for comparison.

Further, 100 g of each dispersion used for Samples 1, 2 and 3 was stored at room temperature (25 ± 5° C.) for 4 weeks, then heated to 45° C. and filtered using a Toyo Filter Paper No. 3. The weight of the residue remaining on the filter paper is shown below.

| | Residue (g) |
|---|---|
| Dispersion 1 | 0 |
| Dispersion 2 | 0 |
| Dispersion 3 | 2 |

From the above results it can be seen that superior stability during storage of the dispersion containing the combination of the compound of the general formula (I) with the phenolic compound according to the present invention is obtained.

EXAMPLE 2

In the same manner as described in Example 1, dispersions were prepared using the compounds shown in Table 2 below and the same subsequent procedures as described in Example 1 were used to prepare Samples 4 to 7.

Table 2

| Sample | Coupler | Solvent | Color Image Stabilizer | Hydroquinone Derivative |
|---|---|---|---|---|
| 4 | Coupler in Example 1 | Dioctyl Butyl Phosphate: 10 ml Ethyl Acetate: 20 ml | Phenolic Compound PH-6: 2 g | Compound prepared in Synthesis Example 1: 2 g |
| 5 | " | " | " | 2,5-Di-tert-octylhydroquinone: 2 g |

Table 2-continued

| Sample | Coupler | Solvent | Color Image Stabilizer | Hydroquinone Derivative |
|---|---|---|---|---|
| 6 | " | Dioctyl Butyl Phosphate: 5 ml Ethyl Acetate: 10 ml | Phenolic Compound PH-4: 2 g | Compound prepared in Synthesis Example 1: 2 g |
| 7 | " | " | " | 2,5-Di-tert-octylhydroquinone: 2 g |

The samples were exposed and processed in the same manner as described in Example 1 to form color dye images and were subjected to a fading test using a fluorescent lamp fading tester (20,000 lux) equipped with an ultraviolet light-absorbing filter absorbing light of a wavelength of 400 nm or shorter (made by Fuji Photo Film Co., Ltd.). The results obtained are shown in Table 3 below.

Table 3

| Sample | Yellow Density Change in Background Areas | Magenta Density Change in Areas of Initial Density 1.0 |
|---|---|---|
| 4* | +0.04 | −0.15 |
| 5** | +0.10 | −0.25 |
| 6* | +0.06 | −0.20 |
| 7** | +0.12 | −0.40 |

*Present Invention
**For Comparison

From the results shown above, it is apparent that Samples 4 and 6 according to the present invention are excellent in view of the discoloration of background areas and the fastness of the color images.

EXAMPLE 3

In the same manner as described in Example 1, the first layer (undermost layer) to the sixth layer (uppermost layer) as shown below were coated on a polyethylene laminated paper to prepare a multilayer color light-sensitive material (in the table below, the designation "mg/m$^2$" is the amount coated). The dispersion used in the third layer of Samples 8 and 9 had the components shown in Table 4 and was prepared in the same manner as described in Example 1.

| Layer | Composition |
|---|---|
| Sixth Layer: | Gelatin 1,000 mg/m$^2$ |
| Fifth Layer | Red-Sensitive Layer (RL) Silver halide emulsion AgBrCl (Br: 50 mol%); Silver 200 mg/m$^2$; Cyan coupler*$^1$ 400 mg/m$^2$; Gelatin 1,000 mg/m$^2$; Coupler solvent*$^2$ 200 mg/m$^2$ |
| Fourth Layer: | Gelatin 1,200 mg/m$^2$; Ultraviolet light-absorbing agent 1,000 mg/m$^2$ |
| Third Layer: | Green-Sensitive Layer (GL) Silver halide emulsion AgBrCl (Br: 50 mol%); Silver 400 mg/m$^2$; Magenta coupler*$^3$ 300 mg/m$^2$; Color image stabilizer*$^7$; Coupler solvent*$^4$ 300 mg/m$^2$ |
| Second Layer: | Gelatin 1,000 mg/m$^2$, Dioctyl hydroquinone 50 mg/m$^2$ |
| First Layer | Blue-Sensitive Layer (BL) Silver halide emulsion AgBrCl (Br: 80 mol%); Silver 400 mg/m$^2$; Gelatin 1,200 mg/m$^2$; Yellow coupler*$^5$ 300 mg/m$^2$; Coupler Solvent*$^2$ 150 mg/m$^2$ |
| Support | Polyethylene laminated paper*$^6$ |

*$^1$Coupler: 2-[α-(2,4-Di-tert-amylphenoxy)butyramido]-4,6-dichloro-5-methylphenol
*$^2$Coupler Solvent: Dibutyl phthalate
*$^3$Coupler: 1-(2,4,6-Trichlorophenyl)-3-(2-chloro-5-tetra-decanamido)anilino-2-pyrazolin-5-one
*$^4$Coupler Solvent: Tricresyl phosphate
*$^5$Coupler: α-Pivaloyl-α-(2,4-dioxo-5,5-dimethyloxazolidin-3-yl)-2-chloro-5-[α-(2,4-di-tert-amylphenoxy)butanamido]-acetanilide
*$^6$Paper support, both sides of which were laminated with polyethylene containing titanium dioxide dispersed therein
*$^7$See Table 4 below.

Table 4

| Sample | Color Image Stabilizer | Hydroquinone Derivative |
|---|---|---|
| 8 | PH-2 | 60 mg/m$^2$ | 2,5-Di-tert-octyl Hydroquinone 60 mg/m$^2$ |
| 9 | PH-2 | 60 mg/m$^2$ | Compound prepared in Synthesis Example 1 60 mg/m$^2$ |

These samples were subjected to the same processing as described in Example 1 and to the fading testing for 6 weeks using the fluorescent lamp fading tester (20,000 lux). The results obtained are shown in Table 5 below.

Table 5

| Sample | Yellow Density Change in Background Areas | Magenta Density Change in Areas of Maximum Density |
|---|---|---|
| 8 | +0.15 | −0.60 |
| 9 | +0.05 | −0.30 |

From the results shown above, it is apparent that the combination according to the present invention results in lesser change in yellow density of the background areas and a superior stabilizing property to color images.

While the invention has been described in detail and with reference to specific embodiments thereof, it will be apparent to one skilled in the art that various changes and modifications can be made therein without departing from the spirit and scope thereof.

What is claimed is:

1. A color photographic silver halide light-sensitive material comprising a support having thereon a silver halide photographic emulsion layer having a dye image providing material associated therewith and with the light-sensitive material containing an isomeric mixture of compounds represented by the following general formula (I) or precursors thereof:

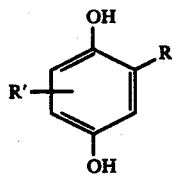  (I)

wherein R and R', which may be the same or different, each represents

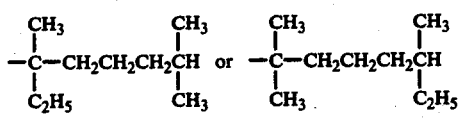

and at least one non-coupling phenolic compound having an ether bond at the 4-position thereof.

2. The color photographic light-sensitive material as claimed in claim 1, wherein said phenolic compound is an alkoxyphenol, an aryloxyphenol, a hydroxycoumaran, a hydroxychroman or a dihydroxyspirochroman.

3. The color photographic light-sensitive material as claimed in claim 1, wherein said phenolic compound is a compound represented by the following general formula (IIa), (IIb) or (IIc):

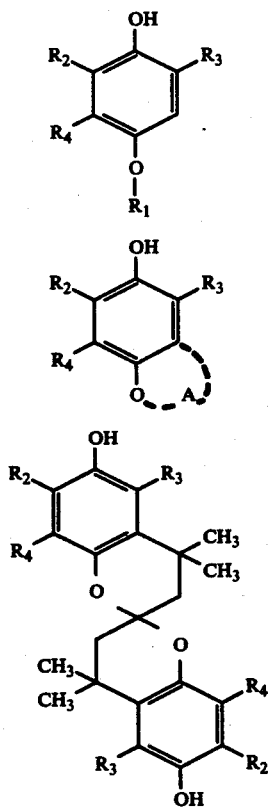

wherein $R_1$ represents a straight chain, branched chain or cyclic alkyl group; a substituted straight chain or branched chain alkyl group; a mono- or bicyclic aryl group; an aralkyl group in which the aryl moiety is a monocyclic aryl moiety and the alkyl moiety is a straight chain or branched chain alkyl moiety; or a terphenyl group; $R_2$, $R_3$ and $R_4$, which may be the same or different, each represents a hydrogen atom; a straight chain, branched chain or cyclic alkyl group; a straight chain or branched chain alkoxy group; a straight chain or branched chain alkylthio group; a monocyclic aryl group; a monocyclic aryloxy group; an aralkyl group in which the aryl moiety is a monocyclic aryl moiety and the alkyl moiety is a straight chain or branched chain alkyl moiety; an aralkoxy group in which the aryl moiety is a monocyclic aryl moiety and the alkyl moiety is a straight chain or branched chain alkyl moiety; a straight chain or branched chain alkenyl group; a straight chain or branched chain alkenoxy group; an acylamino group; or a halogen atom; and A represents the non-metallic atoms necessary for completing a 5-membered or 6-membered ring containing a

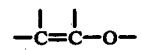

grouping and the ring can be substituted with a straight chain, branched chain or cyclic alkyl group; a straight chain or branched chain alkoxy group; a monocyclic aryl group; a monocyclic aryloxy group; an aralkyl group in which the aryl moiety is a monocyclic aryl moiety and the alkyl moiety is a straight chain or branched chain alkyl moiety; an aralkoxy group in which the aryl moiety is a monocyclic aryl moiety and the alkyl moiety is a straight chain or branched chain alkyl moiety; a straight chain or branched chain alkenyl group; a straight chain or branched chain alkenoxy group; an N-substituted amino group; or a heterocylic ring, which may be substituted with a residue forming a condensed ring; and wherein the alkyl group and the aryl group as described above for $R_1$ and $R_4$ and the alkyl moiety and aryl moiety described for $R_1$ to $R_4$ can be substituted with one or more of a halogen atom, a hydroxyl group, a carboxyl group, an alkoxycarbonyl group, an acyloxy group, a carbamoyl group, a sulfo group, a sulfonyloxy group, an amido group, an alkoxy group or an aryloxy group.

4. The color photographic light-sensitive material as claimed in claim 3, wherein said phenolic compound is a 5-hydroxycoumaran or a 6-hydroxychroman having the general formula (IIb) wherein one of $R_2$ and $R_3$ is a hydrogen atom or a 6,6'-dihydroxy-bis-2,2'-spirochroman having the general formula (IIc).

5. The color photographic light-sensitive material as claimed in claim 1, wherein said dye image providing material is a color coupler and said color coupler is present in said silver halide photographic emulsion layer.

6. The color photographic light-sensitive material as claimed in claim 5, wherein said color coupler is a magenta coupler.

7. The color photographic light-sensitive material as claimed in claim 6, wherein said magenta coupler is a compound represented by the following general formula (III) or (IV):

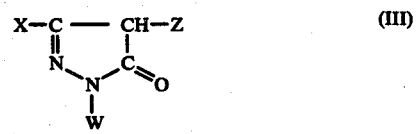

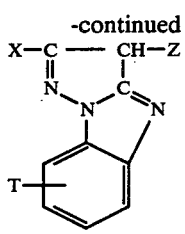

(IV)

wherein

W represents a hydrogen atom or has up to 35 carbon atoms and represents a straight chain or branched chain alkyl group, an alkenyl group, a cycloalkyl group, an aralkyl group and a cycloalkenyl group, which groups can be substituted with one or more of a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group and a mercapto group as substituents; an aryl group which may be substituted with one or more of an alkyl group, an alkenyl group, a cycloalkyl group, an aralkyl group, a cycloalkenyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, a diacylamino group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group and a mercapto group as substituents; or a heterocyclic group containing one or more of a nitrogen atom, an oxygen atom or a sulfur atom as a hetero atom, which may be condensed with another ring and/or which may be substituted with one or more of the substituents above-described for the aryl group for W; an acyl group; a thioacyl group; an alkylsulfonyl group; an arylsulfonyl group; an alkylsulfinyl group; a carbamoyl group or a thiocarbamoyl group;

X represents a hydrogen atom or has up to 35 carbon atoms and represents a straight chain or branched chain alkyl group, an alkenyl group, a cycloalkyl group, an aralkyl group and a cycloalkenyl group, which groups may be substituted with one or more substituents as above-described for W; an aryl group as described above for W, which can be substituted with one or more substituents as described above for W; or a heterocyclic group as described above for W, which can be substituted with one or more substituents as described above for W; an alkoxycarbonyl group; an aryloxycarbonyl group; an aralkyloxycarbonyl group; an alkoxy group; an aryloxy group; an alkylthio group; an arylthio group; a carboxy group; an acylamino group; a diacylamino group; an N-alkylacylamino gruoup; an N-arylacylamino group; a ureido group; a thioureido group; a urethane group; a thiourethane group; an anilino group; an alkylamino group; a cycloamino group; an alkylcarbonyl group; an arylcarbonyl group; a sulfonamido group; a carbamoyl group; a sulfamoyl group; a guanidino group; a cyano group; an acyloxy group; a sulfonyloxy group; a hydroxy group; a mercapto group; a halogen atom or a sulfo group;

T represents a hydrogen atom or has up to 35 carbon atoms and represents a straight chain or branched chain alkyl group, an alkenyl group, a cycloalkyl group, an aralkyl group, and a cycloalkenyl group, which can be substituted with one or more substituents as described above for these groups for W; an aryl group as described above for the aryl group for W and which can be substituted with one or more substituents as described above for W; a heterocyclic group as described above for the heterocyclic group for W and which can be substituted with one or more substituents as described above for W; a halogen atom; a cyano group; an alkoxy group; an aryloxy group; a carboxy group; an alkoxycarbonyl group; an aryloxycarbonyl group; an acyloxy group; an alkylcarbonyl group; an arylcarbonyl group; an alkylthiocarbonyl group; an arylthiocarbonyl group; a sulfo group; a sulfamoyl group; a carbamoyl group; an acylamino group; a diacylamino group; a ureido group; a thioureido group; a urethane group; a thiourethane group; a sulfonamido group; an alkylsulfonyloxy group; an arylsulfonyloxy group; an arylsulfonyl group; an arylthio group; an alkylthio group; an alkylsulfinyl group; an arylsulfinyl group; an alkylamino group; a dialkylamino group; an anilino group; an N-arylanilino group; an N-alkylanilino group; an N-acylaniline group; a hydroxy group or a mercapto group; and Z represents a hydrogen atom or a group bonded directly to the coupling position and capable of being released by a coupling reaction with an oxidation product of a primary amine developing agent.

8. The color photographic silver halide light-sensitive material as claimed in claim 1, wherein said compound represented by the general formula (I) or said precursor thereof and said phenolic compound are present in a silver halide emulsion layer, a protective layer, a yellow filter layer, a halation-preventing layer, a subbing layer, an intermediate layer or a color diffusion transfer positive layer.

9. A color photographic silver halide light-sensitive material comprising a support having thereon a blue-sensitive silver halide emulsion layer containing a yellow coupler, a green-sensitive silver halide emulsion layer containing a magenta coupler and a red-sensitive silver halide emulsion layer containing a cyan coupler, said green-sensitive silver halide emulsion layer containing an isomeric mixture of compounds represented by the following general formula (I) or precursors thereof

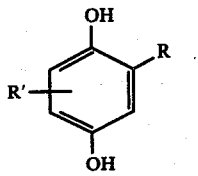

wherein R and R', which may be the same or different, each represents

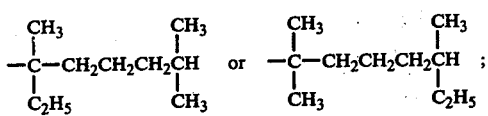

and at least one non-coupling phenolic compound having an ether bond at the 4-position thereof.

10. The color photographic silver halide light-sensitive material as claimed in claim 9, wherein said magenta coupler is a 1-aryl-3-anilino-2-pyrazolin-5-one coupler and the phenolic compound is

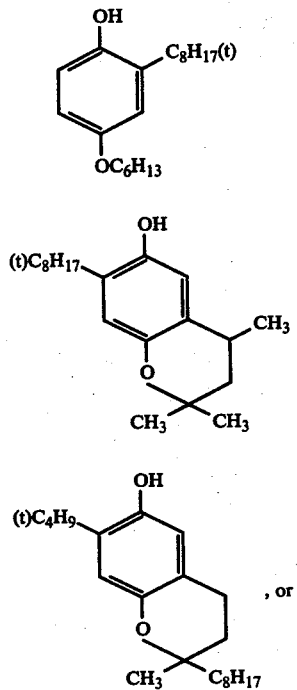

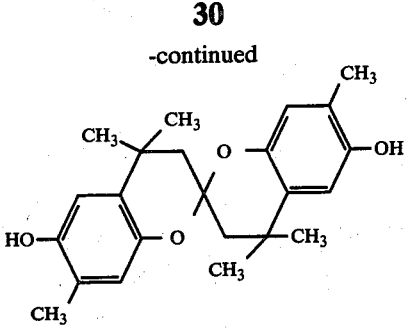

11. The color photographic silver halide light-sensitive material as claimed in claim 1, wherein the molar ratio of the compound represented by the general formula (I) to the phenolic compound ranges from about 0.1:1 to about 10:1.

12. The color photographic silver halide light-sensitive material as claimed in claim 11, wherein the molar ratio of the compound represented by the general formula (I) to the phenolic compound ranges from 0.2:1 to 5:1.

13. The color photographic silver halide light-sensitive material as claimed in claim 1, wherein one of the isomers in said isomeric mixture is 2,5-bis(1-ethyl-1,5-dimethylhexyl)hydroquinone.

14. The color photographic silver halide light-sensitive material as claimed in claim 1, wherein one of the isomers in said isomeric mixture is 2,5-bis(1,1,5-trimethylheptyl)hydroquinone.

15. The color photographic silver halide light-sensitive material as claimed in claim 1, wherein one of the isomers in said isomeric mixture is 2(1-ethyl-1,5-dimethylhexyl)-5-(1,1,5-trimethylheptyl)hydroquinone.

16. The color photographic silver halide light-sensitive material as claimed in claim 9, wherein one of the isomers in said isomeric mixture is 2,5-bis(1-ethyl-1,5-dimethylhexyl)hydroquinone.

17. The color photographic silver halide light-sensitive material as claimed in claim 9, wherein one of the isomers in said isomeric mixture is 2,5-bis(1,1,5-trimethylheptyl)hydroquinone.

18. The color photographic silver halide light-sensitive material as claimed in claim 9, wherein one of the isomers in said isomeric mixture is 2(1-ethyl-1,5-dimethylhexyl)-5-(1,1,5-trimethylheptyl)hydroquinone.

19. The color photographic silver halide light-sensitive material as claimed in claim 1, wherein said isomeric mixture is a mixture of compounds of said general formula (I) wherein the alkyl group in one isomer is a 1,1,5-trimethylheptyl group and the alkyl group in the other isomer is 1-ethyl-1,5-dimethylhexyl group.

20. The color photographic silver halide light-sensitive material as claimed in claim 9, wherein said isomeric mixture is a mixture of compounds of said general formula (I) wherein the alkyl group in one isomer is a 1,1,5-trimethylheptyl group and the alkyl group in the other isomer is 1-ethyl-1,5-dimethylhexyl group.

* * * * *